United States Patent
Spieksma

(10) Patent No.: US 6,711,532 B1
(45) Date of Patent: Mar. 23, 2004

(54) METHOD AND APPARATUS FOR PREDICTING A DISTILLATION TEMPERATURE RANGE OF A HYDROCARBON-CONTAINING COMPOUND

(75) Inventor: Walter Spieksma, Haarlem (NL)

(73) Assignee: A.C. Analytical Controls Holding, B.V., Rotterdam (NL)

( * ) Notice: Subject to any disclaimer, the term of this patent is extended or adjusted under 35 U.S.C. 154(b) by 364 days.

(21) Appl. No.: 09/711,180

(22) Filed: Nov. 13, 2000

Related U.S. Application Data

(63) Continuation of application No. 09/528,599, filed on Mar. 20, 2000, which is a continuation of application No. 09/387,592, filed on Aug. 31, 1999, now abandoned.

(30) Foreign Application Priority Data

Sep. 1, 1998 (EP) ............................................. 98202910

(51) Int. Cl.⁷ ............................. G06G 7/48; G06G 7/58; B01D 15/00
(52) U.S. Cl. ............................ 703/12; 703/11; 210/664
(58) Field of Search .................... 703/11, 12; 210/664

(56) References Cited

U.S. PATENT DOCUMENTS 4,757,023 A 7/1988 Trestianu et al.
4,971,915 A 11/1990 Schwartz et al.

FOREIGN PATENT DOCUMENTS

EP 0833155 A1 1/1998

OTHER PUBLICATIONS

Author: Walter Spieksma; Title: "Prediction of ASTM Method D86 Distillation of Gasolines and Naphthas according to the Fugacity–Filmmodel from Gas Chromatographic Detailed Hydrocarbon Analysis" 36(9): 467–475; Date of Publication: Sep. 1998; Place of Publication: Unknown.

*Primary Examiner*—Hugh Jones
(74) *Attorney, Agent, or Firm*—Hoffmann & Baron, LLP

(57) ABSTRACT

A method and apparatus for predicting a distillation temperature range of a hydrocarbon-containing compound comprising gasoline and/or naphta. The said hydrocarbon-containing compound is analyzed and specific parameters of interest are determined. The values of said determined parameters of interest are processed in a predetermined mathematical distillation model. From said model the distillation temperature range of said hydrocarbon-containing compound is calculated and data representing the result of said calculation are produced.

11 Claims, 4 Drawing Sheets

METHOD AND APPARATUS FOR PREDICTING A DISTILLATION TEMPERATURE RANGE OF A HYDROCARBON-CONTAINING COMPOUND

This application is a continuation of U.S. application Ser. No. 09/528,599 filed on Mar. 20, 2000 which is a continuation application of U.S. application Ser. No. 09/387,592 filed on Aug. 31, 1999 now abandoned.

BACKGROUND OF THE INVENTION

The present invention relates to a method and an apparatus for predicting a distillation temperature range of a hydrocarbon-containing compound.

It is generally known in petrochemical industry to perform a distillation analysis of a hydrocarbon-containing compound such as a petroleum product (e.g. gasoline and/or naphta) in order to obtain distillation data such as boiling point range and the like.

Such a distillation is usually performed according to an ASTM method, in particular the ASTM D 86 distillation method. ASTM methods are standard test methods for petroleum products, are known to those skilled in the art and will therefore not be described in detail. ASTM D 86 is a standard test method for distillation of petroleum products and covers the distillation of natural gasolines, motor gasolines, aviation gasolines, aviation turbine fuels, special boiling point spirits, naphtas, white spirit, kerosines, gas oils, distillate fuel oils, and similar petroleum products, utilizing either manual or automated equipment. ASTM stands for American Society for Testing and Materials.

Summarizing it can be said that a predetermined volume sample of a hydrocarbon-containing compound (e.g. 100 ml) is distilled under prescribed conditions. Systematic observations of thermometer readings and volumes of condensate are made and from this data, results of the test are calculated and reported.

However, in practice the well-known ASTM D 86 method is time-consuming and rather complicated and its results are subject to undesirable variations.

Therefore, there is a need to replace ASTM D 86 distilation by an analysis such as gaschromatography (GC) which offers much more compositional detail and requires less operator time per sample. However, the pure component boiling points of separated GC peaks differ in nature from D 86 boiling points and it has appeared very difficult to link GC data to distillation performance in a satisfactory manner.

Generally, a GC-analysis is performed, e.g. according to the well-known ASTM method D 2887, producing temperature/volume data, which are converted to ASTM D 86 distillation data by statistical techniques, e.g. a set of correlations.

Calculations are performed by any data processing means suitable for the purpose such as a computer.

The disadvantage of a correlation is, however, that erroneous results cannot be understood.

Further, the use of a set of correlations may show results subject to variations with the season of the year and the blending of the sample.

While the ability of GC in order to measure mixture composition is superior to other techniques, the statistical approach, however, fails to predict these variations.

Therefore, a strong need exists for a method and apparatus for predicting the distillation temperature range of a hydrocarbon-containing compound in a reliable manner without the requirement to carry out an experimental ASTM D 86 distillation method or applying correlation techniques in GC analysis.

It is now an object of the present invention to fulfil this need.

SUMMARY OF THE INVENTION

The present invention therefore provides a method for predicting a distillation temperature range of a hydrocarbon-containing compound comprising gasoline and/or naphta, said method comprising the steps of:

a) analyzing the said hydrocarbon-containing compound and determining specific physico-chemical parameters of interest;

b) processing the values of said determined parameters of interest in a predetermined mathematical distillation model;

c) calculating from said model the distillation temperature range of said hydrocarbon-containing compound; and d) producing data representing the result of said calculating step c).

The present invention further provides an apparatus for predicting a destination temperature range of a hydrocarbon-containing compound comprising gasoline and/or naphta, said apparatus comprising a means for analyzing the said hydrocarbon-containing compound and determining specific physico-chemical parameters of interest; means for processing the values of said determined parameters of interest in a predetermined mathematical distillation model; means for calculating from said model the distillation temperature range of said hydrocarbon-containing compound; and means for producing data representing the result of the calculation.

In this manner a simple and time-saving method and apparatus have been provided to obtain petroleum product distillation parameters of interest. In particular an accurate simulation of the ASTM D 86 method can be obtained by the method and apparatus according to the present invention by processing the results from an analysis of the hydrocarbon-containing compound in a mathematical model.

In this manner, carrying out the difficult time-consuming and complicated experimental ASTM D 86 distillation method or applying unreliable sets of correlations in GC analysis is made superfluous.

BRIEF DESCRIPTION OF THE DRAWINGS

The invention will now be explained in more detail by way of example by reference to the accompanying drawings, in which.

DESCRIPTION OF THE PREFERRED EMBODIMENTS

Figure 1:
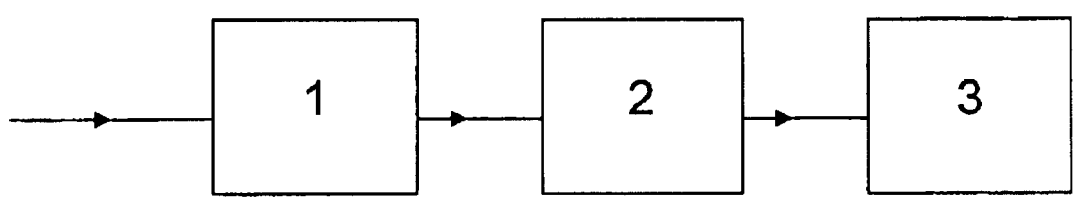
FIG. 1 is a block diagram of the process according to the invention.

Referring to FIG. 1 a hydrocarbon-containing compound is supplied to and analyzed in any suitable analyzer 1 and specific physico-chemical parameters of interest are determined (step 1). The values of these determined parameters of interest are processed in a predetermined mathematical distillation model (2) and from said model the distillation temperature range of the hydrocarbon-containing compound under investigation is calculated by a data processing means such as a computer and the data representing the calculation results are produced and recorded on any display device suitable for the purpose (3).

Advantageously, the mathematical distillation model is a non-equilibrium transport model, e.g. a fugacity-filmmodel of interphase transport.

Advantageously, step 1 is carried out by detailed hydrocarbon analysis (DHA), and in particular by gas chromatographic analysis or gas-liquid chromatographic analysis. DHA as such is known to those skilled in the art and can be defined as temperature-programmed capillary gas chromatography.

In this step an undiluted volatile sample is sealed in a crimp-cap vial. The vial is placed in an autosampler, and a microliter volume of sample is withdrawn and injected into the gas chromatograph (GC). The GC is equipped with a split/splitless injector, a capillary column and a flame ionization detector (FID). The split ratio and injected volume should be adjusted to obtain symmetrical GC peaks. The GC oven is temperature programmed and column dimensions and carrier gas velocity should be optimized to obtain separation of the (target) components. In principle, any detector that can determine the following three input data of the transport model: (1) peak identity, (2) weight or volume fraction and (3) retention time or Kovats index may be used. Kovats indices are calculated from retention times relative to the n-Paraffins. Identification of peaks is performed by matching retention time or Kovats index with a database. Weight % is calculated from peak area using theoretical response factors, based on Hydrogen/Carbon ratio of the identified peak.

The chromatogram is integrated to determine area and retention time of the peaks. Typical chromatograms of Naphthas, Gasolines or blendstocks display hundreds of peaks. Above 257 peaks, the small, unidentified peaks are lumped to obtain a maximum of 257 components. At least 50% of the sample should be identified, including the largest and well-separated peaks at the light end of the chromatogram. The integration settings should be chosen such that the small peaks at the heavy end of the chromatogram are included in the report. Analysis time can vary from around 20 minutes (narrow bore) to several hours. Operator time per sample is minimized and unattended analysis may be performed by virtue of the autosampler.

The above parameters (peak area and retention time) are applied as input to the transport model.

The transport model uses the quantitative and qualitative information generated by the (GC) to simulate the ASTM method D86 distillation. First, physical properties of all the components (GC peaks) are calculated. Mole fractions are calculated from GC weight fractions, using molar mass of the components. Bubble lines are calculated from the GC Kovats inded of the components. Mixture activity and diffusion coefficients are calculated and applied in the fugacity-filmmodel, based on Henry's law and Fick's law. The approach according to the present invention is new in that up to now only correlations were used to convert GC data to ASTM D 86 data. The model approach of the present invention is capable of adjusting setpoints and evaluating blends, whereas the correlation technique is not generally applicable.

Figure 2:
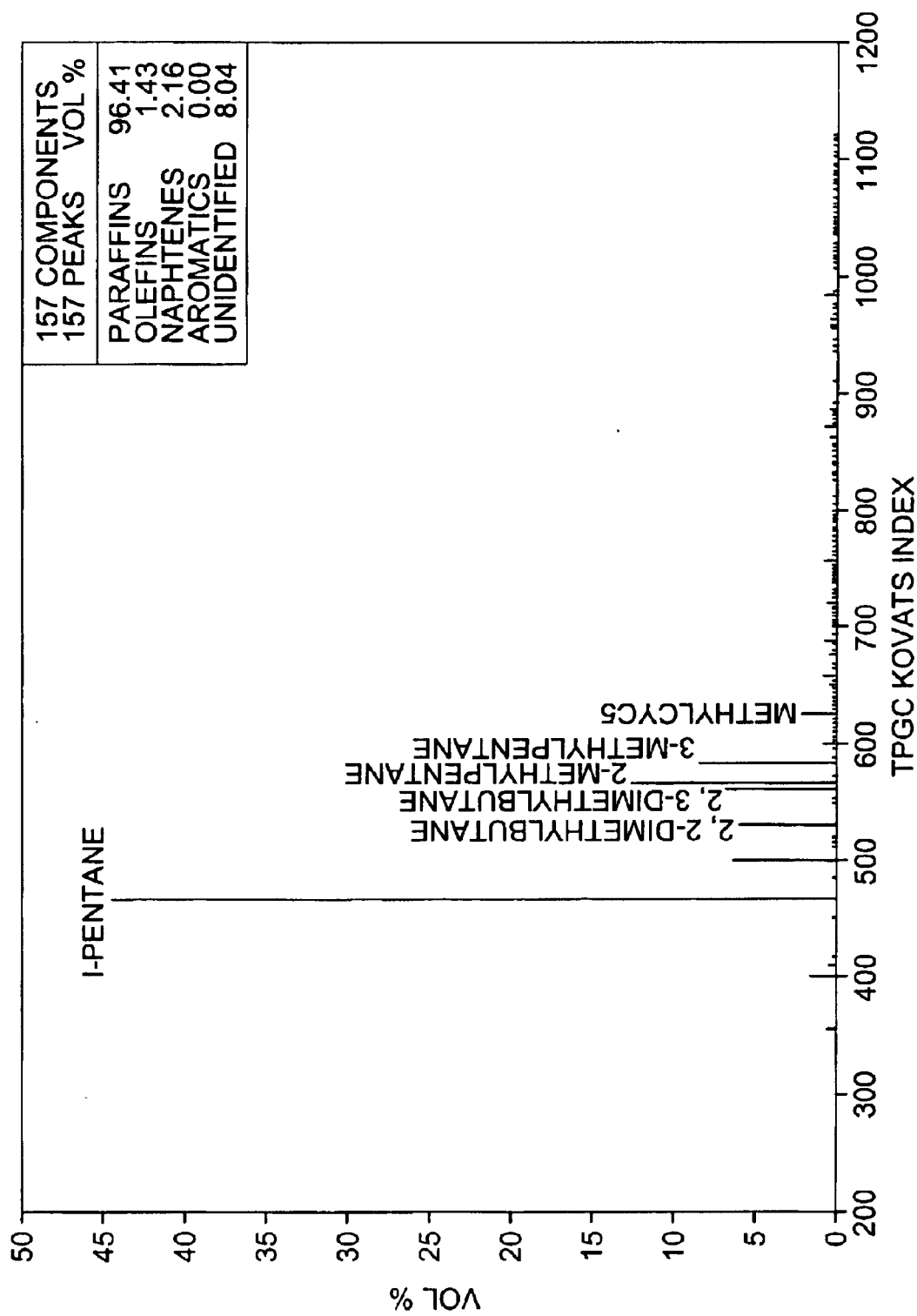
FIGS. 2–4 represent examples of chromatograms obtained by the method according to the present invention.
Figure 3:
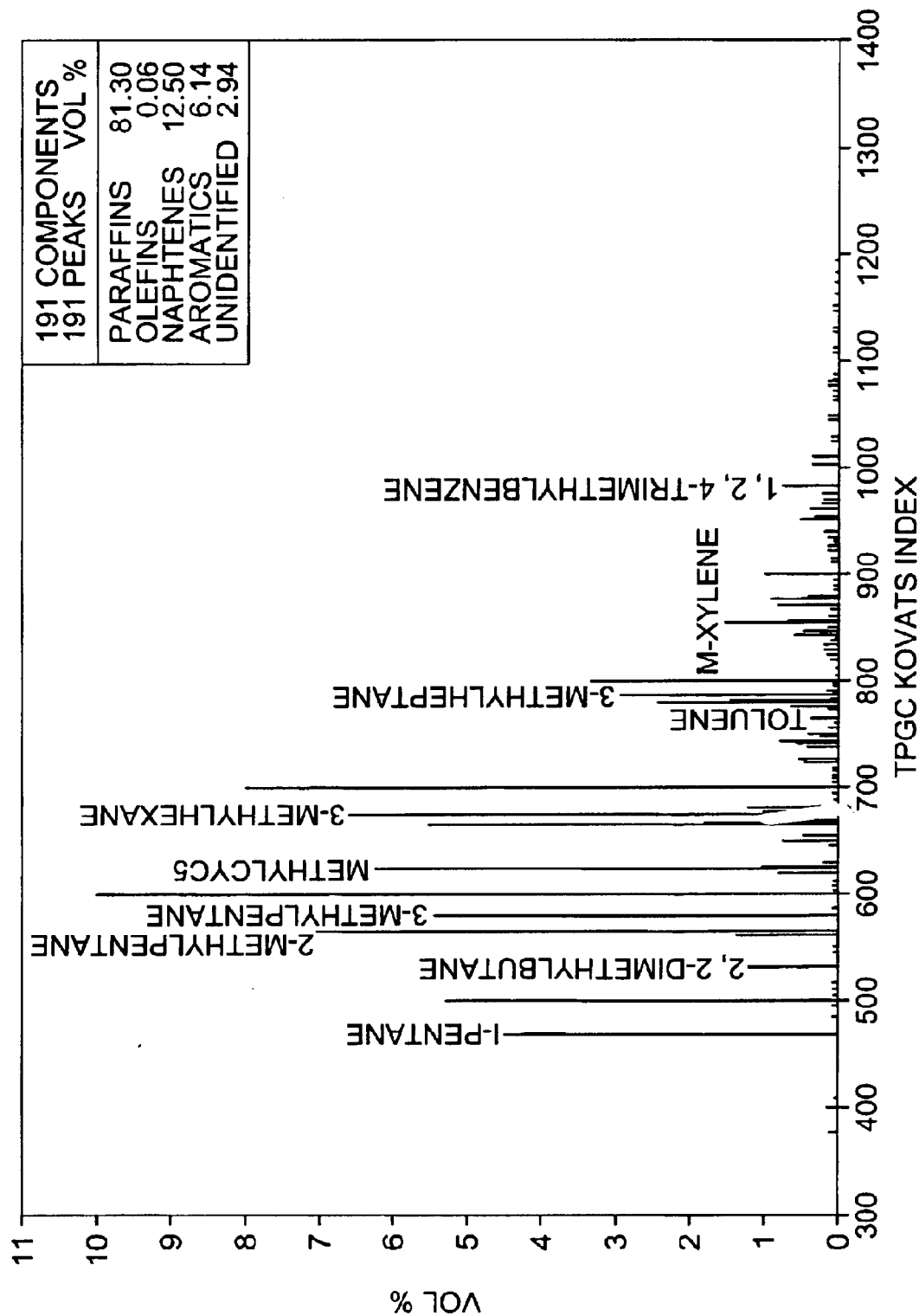
Figure 4:
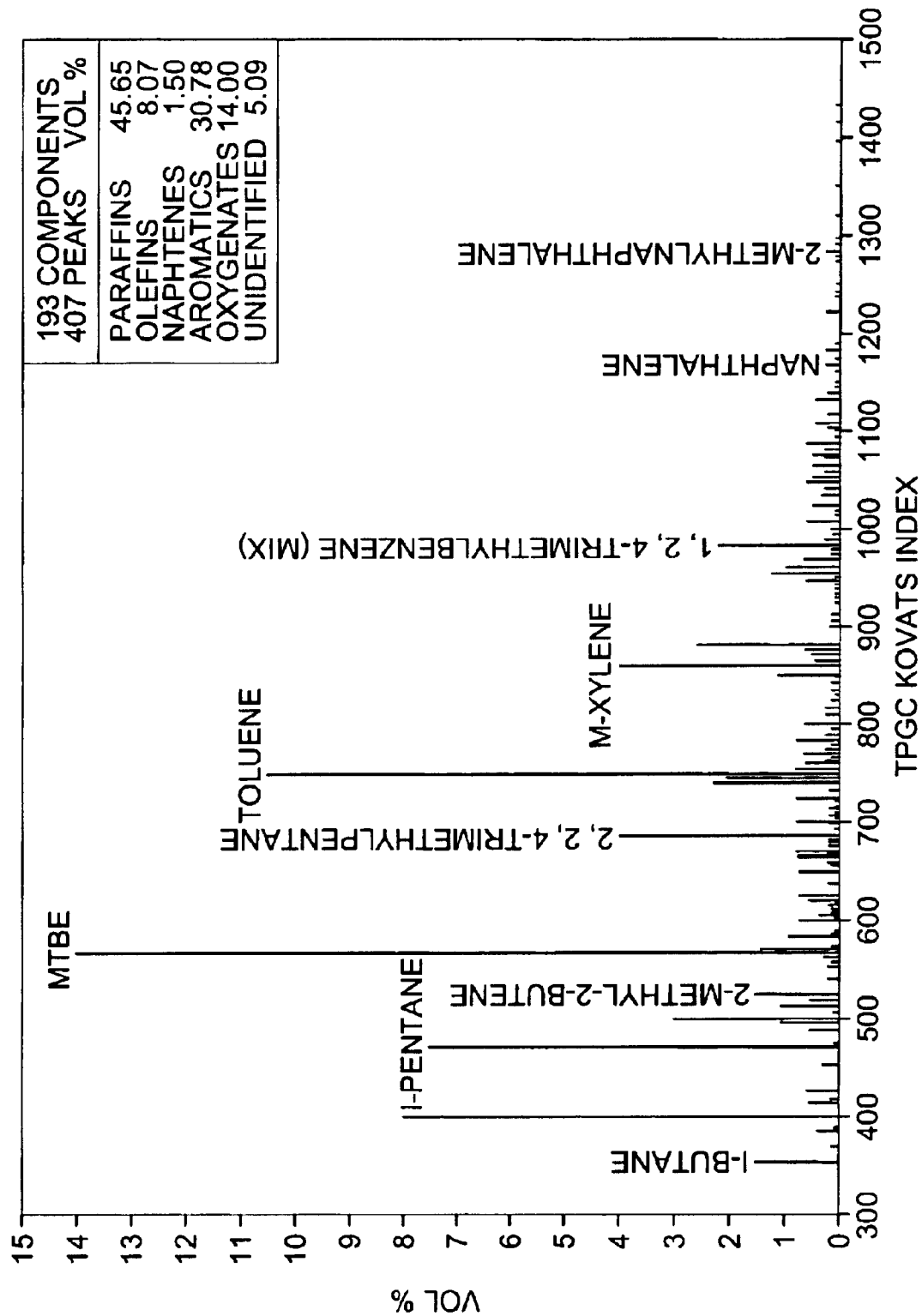

In FIGS. 2–4 chromatograms are represented in volume % and Kovats index bar graphs.

The obtained Kovats indices and mole fractions of the components are now used in a mathematical model such as the fugacity-filmmodel, obtained from the combination of Fick's and Henry's law.

From this model temperature/volume data are calculated and produced in any way suitable for the purpose.

EXAMPLES

The present invention will now be described in more detail by reference to the following example.

Isomerate and raffinate samples have been analyzed according to a DHA method. The samples were analyzed without dilution. Small injection volumes (0.1 μl) and a split ratio of 200:1 were employed.

By means of DHA peaks were obtained, which are identified with the Kovats index. The theoretical FID response factor, given in ASTM method D 5443, was calculated from the carbon/hydrogen ratio in the molecule. Weight fractions were calculated from areas of all peaks and the theoretical response factors. These parameters were fed as an input to a mathematical fugacity-filmmodel. The output of the said model provides a simulation of the ASTM D 86 method. Density and molar mass were used to calculate volume and mole fractions respectively.

The mathematical fugacity-filmmodel of interphase mass transport, which is known as such to those skilled in the art, is based upon the following:

Fugacity is the tendency of a component to escape from its phase compartment. The dimension of fugacity is force per area or Pascal ($N/m^2$). At equilibrium between liquid and vapor in a closed system, fugacities of all components in the liquid and gas phase are equal. Using Dalton's law the fugacity of component i in the vapor-phase (G) is defined:

$$f_i^G = y_{i-\gamma i} P \quad [Pa] \quad (1)$$

Gas phase fugacity corresponds to partial pressure, which is the product of component (i) mole fraction ($y_i$) and total pressure (P). The fugacity of component i in the liquid phase (L) is defined:

$$f_i^L = y_i^L x_i P^i \quad [Pa] \quad (2)$$

Henry's law is found at equilibrium between vapor and liquid phase, when Eq. (1) equals Eq. (2):

$$y_i P = y_i^L x_i P^i \quad [Pa] \quad (3)$$

The liquid mole fraction $x_1$ is obtained from DHA. Pure liquid vapor pressure ($P^l$) is calculated from the Kovats index which is also obtained from DHA. The activity coefficient ($\gamma^L_1$) is calculated according to the Wilson equation for mixtures of N components.

$$\ln y_i^L = 1 - \ln\left(\sum_j^N x_j \Lambda_{ij}\right) - \sum_k \frac{x_k \Lambda_{ki}}{\sum_j^N x_j \Lambda_{kj}} \quad (4)$$

The N×N matrix of Wilson binary parameters (Λ) is calculated from Kovats indices. Despite the fact that Eq. (4) is the least complicated of available mixing equations, computing time rises steeply with the number of components. If Eq. (4) is written out for a mixture of 100 components, 100 denominators appear with 100 terms.

The fugacity-filmmodel of interphase mass transport combines fugacity (Eqns. 1 and 2) and diffusion and is based on three principles:

1. Fick's law states that the flux ($J_1$) of component i through a plane of thickness $\partial_z$ is driven by concentration difference ($\partial C_1$) and is limited by diffusion ($J_1 = ID$, $\partial C_1/\partial z$ (mole/$m^2$s), 2. According to Dalton's law, gas phase concentration is related to vapor mole fraction $y_1$, and total pressure by the formula $C^G_1 = y_1 \, P|RT$ (mole/$m^3$), 3. Lewis defined gas phase fugacity (Eq.1) and liquid phase fugacity (Eq.2) which are equal at equilibrium.

It is assumed that diffusion $ID^L_i$ in a liquid interphase film with thickness δ [m] limits component transport. The resistance if the gas phase is ignored, because diffusion in gases is a factor 1000 faster than in liquids. Then, the evaporation flux $j^L_1$ of component i through area A [m²] can be written as follows:

$$J^L_i = \frac{-\partial n^L_i}{A \partial t} = \frac{ID^L_i}{\delta RT}(f^L_i - f^G_i) \quad [\text{mole}/m^2 s] \quad (5)$$

Both phases are supposed to be well-mixed; no gradients occur in the bulk of the phases. At equilibrium, gas phase fugacity $f^G_1$ ($\leftrightarrows$) equals liquid phase fugacity $f^1_1$, resulting in no flux. In case fugacity $f^G_1$ in the gas-phase is higher than equilibrium fugacity $f^G_1$ ($\leftrightarrows$), condensation of component (i) to the liquid phase will occur according to the negative evaporation flux found by Eq. (5). The liquid film at the exchanging surface area is assumed to be a monomolecular layer of spherical molecules. The interphase liquid film thickness (δ) is calculated from liquid molar volume ($V^2$) of the mixture and the Avogadro number $N_A$ according to: $\delta = 1.204 \sqrt[3]{(V^s|N_A)}$ [m]. Calculation of liquid mixture molar volume is given in the liquid diffusion ($ID^L_1$) calculations.

Determination of exchanging surface area A may be feasible in case of a non-boiling liquid, but is not feasible in the case of a turbulent rising stream of expanding vapor bubbles in a boiling flask e.g. used in ASTM method D 86 distillation.

By applying the method and apparatus according to the present invention obtained chromatograms have been converted in a simple and reliable manner to D 86 distillation curves with the fugacity-filmmodel without the requirement of carrying out the experimental ASTM D 86 test method or applying correlation technique in GC analysis.

It will be appreciated by those skilled in the art that any transport model suitable for the purpose can be used according to the present invention, e.g. the Maxwell-Stephan model, which is known as such to those skilled in the art and, therefore, will not be described in detail.

It will be appreciated that various modifications of the present invention will be apparent to those skilled in the art from the foregoing description. Such modifications are intended to fall within the scope of the appended claims.

What is claimed is:

1. A method for predicting a distillation temperature range of a hydrocarbon-containing compound comprising gasoline and/or naphta, said method comprising the steps of:

a) analyzing said hydrocarbon-containing compound and determining specific physico-chemical parameters of interest;

b) processing the values of said determined parameters of interest in a fugacity-film model of interphase transport;

c) calculating from said model the distillation temperature range of said hydrocarbon-containing compound; and d) producing data representing the result of said calculating step c).

2. The method as claimed in claim 1, wherein step a) is carried out by detailed hydrocarbon analysis (DHA).

3. The method as claimed in claim 1, wherein step c) is carried out by a computer.

4. The method as claimed in claim 1, wherein the data of step d) are boiling point range data.

5. The method as claimed in claim 1, wherein the data produced in step (d) are a simulation of ASTM method D 86.

6. The method as claimed in claim 1, wherein step a) is carried out by gas chromatographic analysis or gas liquid chromatographic analysis.

7. The method as claimed in claim 6, wherein the specific parameters of interest of step (a) are the peak retention time and the peak area.

8. An apparatus for predicting a distillation temperature range of a hydrocarbon-containing compound comprising gasoline and/or naphta, said apparatus comprising a means for analyzing said hydrocarbon-containing compound and determining specific physico-chemical parameters of interest; means for processing the values of said determined parameters of interest in a fugacity-film model of interphase transport; means for calculating from said model the distillation temperature range of said hydrocarbon-containing compound; and means for producing data representing the result of the calculation.

9. The apparatus as claimed in claim 8, wherein said means for analyzing said hydrocarbon-containing compound is a means for detailed hydrocarbon analysis.

10. The apparatus as claimed in claim 8, wherein said means for analyzing said hydrocarbon-containing compound is a gas chromatograph.

11. The apparatus as claimed in claim 8, wherein said means for analyzing said hydrocarbon-containing compound is a gas-liquid chromatograph.

* * * * *

UNITED STATES PATENT AND TRADEMARK OFFICE
CERTIFICATE OF CORRECTION

PATENT NO. : 6,711,532 B1
DATED : March 23, 2004
INVENTOR(S) : Walter Spieksma

It is certified that error appears in the above-identified patent and that said Letters Patent is hereby corrected as shown below:

Column 4,
Line 29, now reads "$f_i^G = y_{i=Y_i}^P$    [Pa] (1)"
should read -- $f_i^G = y_{i=y_i}^P$    [Pa] (1) --

Lines 46-49, now reads "
$$\ln y_i^L = 1 - \ln\left(\sum_i^N x_j \Lambda_{ij}\right) - \sum_k \frac{x_k \Lambda_{ki}}{\sum_j^N x_j \Lambda_{kj}} \qquad (4)$$
"

should read --
$$\ln y_i^L = 1 - \ln\left(\sum_i^N x_j \Lambda_{ij}\right) - \sum_k^N \frac{x_k \Lambda_{ki}}{\sum_j^N x_j \Lambda_{kj}} \qquad (4)$$
--

Signed and Sealed this

Twenty-sixth Day of October, 2004

JON W. DUDAS
*Director of the United States Patent and Trademark Office*

UNITED STATES PATENT AND TRADEMARK OFFICE
CERTIFICATE OF CORRECTION

PATENT NO. : 6,711,532 B2
DATED : March 23, 2004
INVENTOR(S) : Walter Spieksma

It is certified that error appears in the above-identified patent and that said Letters Patent is hereby corrected as shown below:

Column 4,
Line 29, "$f_i^G = y_{i\ =\ Yi} P$ [Pa] (1)" should read -- $f_i^G = y_i P$ [Pa] (1) --

Signed and Sealed this

Eighteenth Day of January, 2005

JON W. DUDAS
*Director of the United States Patent and Trademark Office*